Figure 1:
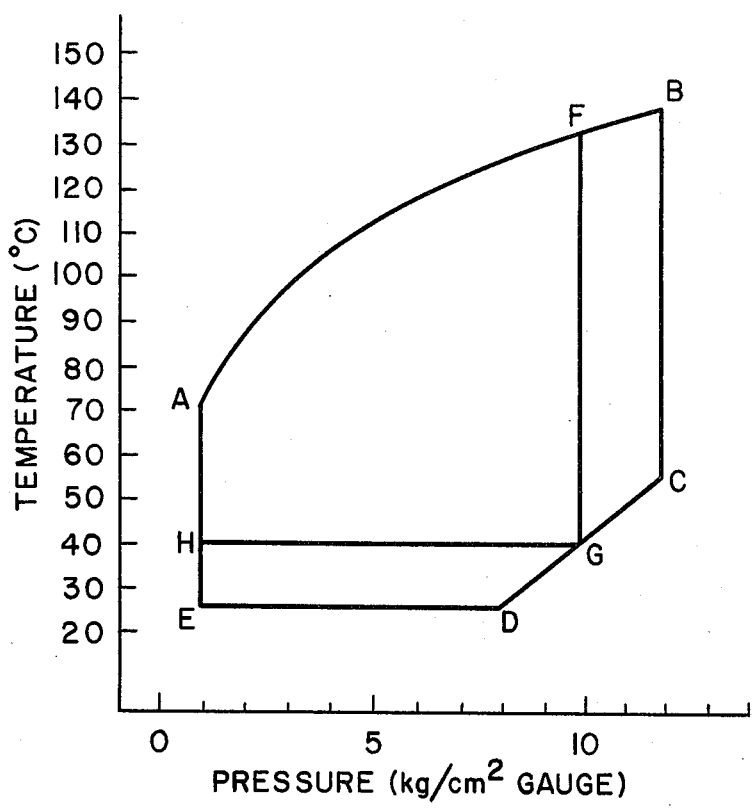

United States Patent [19]

Satokawa et al.

[11] 4,346,250

[45] Aug. 24, 1982

[54] TELOMERIZATION OF TETRAFLUOROETHYLENE

[75] Inventors: Takaomi Satokawa; Tuneo Fujii; Akira Ohmori; Yorio Fujita, all of Osaka, Japan

[73] Assignee: Daikin Kogyo Co., Ltd., Osaka, Japan

[21] Appl. No.: 203,453

[22] Filed: Nov. 3, 1980

[30] Foreign Application Priority Data

Apr. 21, 1978 [JP] Japan .................................. 43-48045

Related U.S. Application Data

[63] Continuation-in-part of Ser. No. 31,843, Apr. 20, 1979, abandoned.

[51] Int. Cl.³ ............................................. C07C 31/38
[52] U.S. Cl. ................................................... 568/842
[58] Field of Search ........................ 568/842; 570/125

[56] References Cited

U.S. PATENT DOCUMENTS

| | | | |
|---|---|---|---|
| 2,559,628 | 7/1951 | Joyce | 568/842 |
| 2,559,629 | 7/1951 | Berry | 568/842 |
| 2,562,547 | 7/1951 | Hanford | 568/842 |
| 3,022,356 | 2/1962 | Ver Nooy | 568/842 |
| 3,157,605 | 11/1964 | Ver Nooy | 568/842 |

Primary Examiner—Werren B. Lone
Attorney, Agent, or Firm—Stevens, Davis, Miller & Mosher

[57] ABSTRACT

Fluoroalkanols of the formula:

$$H(CF_2CF_2)_nCH_2OH \qquad (I)$$

are prepared by telomerization of tetrafluoroethylene with methanol in a batch system. The reaction is carried out while introducing tetrafluoroethylene continuously into the reaction system. The production of fluoroalkanols of the formula (I) wherein n is an integer of 5 or more is suppressed and the production of fluoroalkanols of the formula (I) wherein n is an integer of 4 or less is enhanced.

7 Claims, 3 Drawing Figures

TELOMERIZATION OF TETRAFLUOROETHYLENE

This is a continuation-in-part application of our co-pending application Ser. No. 31,843, filed on Apr. 20, 1979, now abandoned.

The present invention relates to telomerization of tetrafluoroethylene. More particularly, it relates to a process for preparing fluoroalkanols with a relatively low degree of polymerization by telomerization of tetrafluoroethylene with methanol.

For preparation of fluoroalkanols by a batch type telomerization reaction of tetrafluoroethylene (hereinafter referred to as "TFE") with an alkanol, there are known several methods as disclosed in U.S. Pat. Nos. 2,559,628, 2,559,629 and 2,562,547, etc.

According to the method as disclosed in U.S. Pat. No. 2,559,628, methanol (150 parts) and t-butyl octyl peroxide (2 parts) are charged into a high pressure reaction vessel, and, after addition of TFE (110 parts) thereto, the contents are stirred at 170° C. for 10 hours under 90 atm. pressure, whereby the reaction proceeds in the following manner:

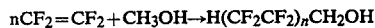

to obtain a mixture of fluoroalkanols with different degrees of polymerization. In this case, the maximum of the value of n is considered to be 12.

Among telomers with various degrees of polymerization obtained from TFE and methanol, only the ones having an n value of not larger than 4 in the above mentioned formula are now utilized industrially, while the telomers having an n value of larger than 4 are not yet employed for practical use. For example, the telomer having an n value of 4 is converted into the corresponding acid by oxidation and utilized as a surface active agent. The telomers having an n value of not larger than 3 are used, solely or in admixture with water, as heat transfer mediums and are also useful as intermediates for preparation of medicines, agricultural chemicals, dyes, color couplers for photographs and surface active agents and as modifying agents and additives for polymers such as polyphosphazene.

Among telomers obtained from TFE and methanol, the demand for the ones having a relatively low molecular weight (especially $n \leq 3$) has been recently increasing. When the telomerization reaction of TFE with methanol is effected according to the process described in the said U.S. patent, the distribution of the molecular weights of the produced telomers is in a wide range, and high molecular weight telomers ($n \geq 5$) which are industrially sustantially useless are inevitably formed as by-products, with industrial disadvantage, in addition to desired low molecular weight telomers.

As the result of the extensive investigation on the conventional processes for batch type telomerization reaction of TFE with methanol, it was found previously that the average molecular weight of the produced telomers could be reduced to some extent by making smaller the molar ratio of TFE and methanol to be charged into the autoclave and keeping higher the reaction temperature. Even in this case, however, formation of a considerably large amount of telomers with an n value of not smaller than 5 is inevitable. Besides, when the moler ratio of TFE and methanol is decreased for preventing formation of high molecular weight telomers, the telomer yield per 1 batch is lowered, which is extremely disadvantageous from the industrial viewpoint.

In Ko Fen Tsu Tung Hsun (W. T. Lin et al.), 6, 363-369 (1964), it is described that the existence of barium oxide or magnesium oxide in the reaction system of batch type telomerization reaction of TFE with methanol increases the reaction rate and the total yield of telomers and at the same time reduces the average molecular weight of produced telomers. According to this method, however, telomers with an n value of not smaller than 4 are unavoidably formed in an amount of about 20 to 30% to the whole amount of produced telomers. This means that a fairly large amount of useless telomers with an n value of not smaller than 5 is contained in the reaction product, on considering the presence of the molecular weight distribution.

Japanese Patent Publication No. 20782/1967 discloses adoption of a continuous process for telomerization of TFE and methanol, in place of a batch process, in which TFE and methanol in a certain proportion are continuously introduced into an end of a reaction tower and at the same time the reaction product is continuously taken out from the other end. According to the working examples in this specification, however, the obtained telomer concentration is small (about 10%) and the average degree of polymerization of the produced telomers becomes extremely large (n=32), the amount of components of $n \leq 4$ being very small.

In U.S. Pat. No. 3,022,356, the telomerization of TFE with methanol by continuous feeding of the starting materials and continuous discharge of the produced telomers is disclosed. However, this method requires a high pressure of about 44 kg/cm$^2$ gauge, and the produced telomers contain those having an n value of 5 or higher a content of about 25%.

As the result of further studies, it has now been found that introduction of TFE into methanol containing a polymerization initiator over a period of time either continuously or in a series of steps can prevent formation of substantially valueless telomers of $n \geq 5$ and to produce useful telomers of $n \leq 4$ predominantly, unlike the product of the batch method in which TFE and methanol are charged into the reaction system from the start and unlike the product of a continuous method in which TFE and methanol are charged continuously and simultaneously.

According to the present invention, a process is provided for preparing fluoroalkanols of the formula: H(CF$_2$CF$_2$)$_n$CH$_2$OH wherein methanol is mixed with a polymerization initiator and tetrafluoroethylene is mixed with the resulting mixture either continuously or intermittently at a temperature of 35° to 150° C. and at a rate whereby the partial pressure ratio of TFE and methanol is between 30/1 to 1/5 and the total pressure on the reaction system is 1 to 12 kg/cm$^2$ gauge. Such a process produces a product wherein n in the above formula is 4 or less and the production of polymers wherein n is 5 or more is suppressed.

The object of the invention can be favorably attained particularly when the telomerization of TFE with methanol is effected by successively, i.e. continuously or intermittently in a series of steps, introducing TFE into methanol containing a polymerization initiator at a temperature of 25° to 150° C. in such a manner that the partial pressure ratio of TFE and methanol becomes from 30/1 to 1/5 and the total pressure of the reaction system becomes 1 to 12 kg/cm$^2$ gauge, and the total pressure and the temperature are kept within the range surrounded by A, B, C, D, and E in FIG. 1 of the accompanying drawings, which will be hereinafter explained.

The first advantageous feature of the invention is that, in comparison with the conventional batch processes, the reaction can be carried out smoothly and safely. In the conventional batch processes, the total amount of TFE to be subjected to the reaction is charged into the reaction vessel from the start, and the reaction is carried out at a temperature of 100° to 250° C., so that the reaction pressure reaches several tens kg/cm$^2$ to even 100 kg/cm$^2$. In addition, the temperature is elevated due to the reaction heat to accelerate the telomerization reaction, which may sometimes cause too rapid progress of the reaction to bring about an explosion. According to the present process, to the contrary, TFE is charged successively under a low pressure, so that the pressure-resistance of the reaction vessel is not required to be so large as in the case of the batch process, and the control of the reaction rate can be effected easily to assure safe operation. The second advantageous feature of the invention is that the average molecular weight of the produced telomers can be optionally and readily regulated within a range of 140 to 300, and formation of industrially valueless telomers having an n value of not less than 5 can be minimized.

In carrying out the process of the invention, a designed amount of methanol and a polymerization initiator are charged into an autoclave equipped with a stirrer, and after eliminating the air in the vessel by a vacuum pump and elevating the temperature up to a designed level by heating, TFE is successively introduced to obtain a designed pressure, whereby a telomerization reaction can proceed smoothly without danger.

As hereinabove stated, the successive introduction of TFE into the reaction system may be carried out continuously or intermittently. In case of continuous introduction, TFE is introduced into the reaction system continuously, i.e. without intermission, so as to maintain the pressure at a pre-determined level. In case of intermittent introduction, TFE is introduced into the reaction system when the pressure is lowered by a certain extent (e.g. 1–2 kg/cm$^2$) from a pre-determined level so as to recover the pre-determined level, and this operation is repeatedly applied.

As the polymerization initiator of the invention, there may be employed any radical-generating agent which does not show telogenic action to TFE. In usual, an azo compound such as azo-bis-isobutyronitrile or a peroxide such as diisopropyl peroxydicarbonate or di-t-butyl peroxide is advantageously employed. Depending on the reaction temperature, a suitable initiator may be selected and incorporated into the reacton system.

For carrying out the process of the invention effectively, the reaction temperature and the pressure are desired to be within the range surrounded by A, B, C, D, and E in FIG. 1 of the accompanying drawings. Especially for obtaining telomers having an optional average molecular weight from 140 to 300, it is preferable to keep the temperature and the pressure within the range surrounded by A, F, G and H.

As an example of the invention, the telomerization reaction of TFE with methanol was effected under the conditions of temperature and pressure within the range of A, B, C, D and E in FIG. 1, and the composition of the thus produced telomer mixture is shown in Table 1.

TABLE 1

| Reaction conditions | | Produced telomers H(CF$_2$CF$_2$)$_n$CH$_2$OH (% by weight) | | | | | | | | | |
|---|---|---|---|---|---|---|---|---|---|---|---|
| temperature (°C.) | Pressure (kg/cm$^2$) | n = 1 | n = 2 | n = 3 | n = 4 | total n ≦ 4 | n = 5 | n = 6 | n = 7 | n = 8 | total n ≧ 5 | Average molecular weight |
| 30 | 4 | 24.1 | 41.2 | 22.4 | 8.6 | 96.3 | 3.0 | 0.6 | 0.1 | — | 3.7 | 259.4 |
| 50 | 2 | 52.0 | 38.2 | 8.5 | 1.1 | 99.8 | 0.2 | — | — | — | 0.2 | 188.7 |
|  | 4 | 37.0 | 41.6 | 16.0 | 4.3 | 98.9 | 1.0 | 0.1 | — | — | 1.1 | 223.0 |
|  | 6 | 25.1 | 41.7 | 22.3 | 8.0 | 97.1 | 2.4 | 0.5 | — | — | 2.9 | 254.1 |
|  | 8 | 21.5 | 38.2 | 23.6 | 10.5 | 93.8 | 4.1 | 1.3 | 0.5 | 0.3 | 6.2 | 276.9 |
| 80 | 4 | 59.0 | 33.5 | 6.5 | 0.8 | 99.8 | 0.2 | — | — | — | 0.2 | 181.5 |
|  | 6 | 43.3 | 41.3 | 12.6 | 2.4 | 99.6 | 0.4 | — | — | — | 0.4 | 267.3 |
|  | 8 | 33.9 | 41.7 | 17.7 | 5.2 | 98.5 | 1.3 | 0.2 | — | — | 1.5 | 230.6 |
|  | 11 | 21.1 | 38.0 | 23.8 | 10.9 | 93.8 | 4.8 | 1.2 | 0.2 | — | 6.2 | 276.5 |
| 110 | 4 | 88.3 | 10.9 | 0.7 | 0.1 | 100 | — | — | — | — | 0 | 144.6 |
|  | 6 | 74.5 | 22.9 | 2.4 | 0.2 | 100 | — | — | — | — | 0 | 160.0 |
|  | 8 | 59.3 | 33.0 | 6.5 | 0.8 | 99.6 | 0.4 | — | — | — | 0.4 | 182.0 |

When the telomerization reaction of TFE with methanol is effected under the reaction conditions of the invention, as apparent from Table 1, the yield of useful telomers of n≦4 reaches 90% or more indeed, and that of valueless high molecular weight telomers of n≧5 can be minimized to several percents or less. It is thus understood that the process of the invention is extremely advantageous from the industrial viewpoint in comparison with the conventional batch process which affords telomers with a large amount of components of n≧5.

According to the process of the invention, it is possible to produce selectively useful telomers from TFE and methanol. When the reaction time is prolonged for increasing the telomer yield in this reaction, the reaction rate is gradually reduced with lapse of time. From the relationship between the temperature and the time in this case, the polymerization initiator is considered to remain in the reaction system in a sufficient amount. As to the cause for the gradual reduction of the reaction rate in spite of the presence of a sufficient amount of the polymerization initiator, it is confirmed that, although the reason is unknown, the pH value of the reaction system is gradually decreased with progress of the reaction and the reaction rate is also reduced with this decrease of the pH value. Namely, the pH value of about 6 at the initial stage of the reaction is gradually decreased with progress of the reaction, and when it becomes about 3, apparent lowering of the reaction rate is observed. By addition of a methanol solution of sodium hydroxide or potassium hydroxide, for instance, into the reaction system for neutralization in this case, the reaction rate is increased to a level approximately equal to the initial rate to permit continuation of the reaction. In the telomerization reaction of TFE with methanol to obtain useful telomers according to the process of the invention, therefore, incorporation of an acid-accepting agent into the reaction system is desirable so as to eliminate acid substances formed and accumulated in the reaction system with progress of the reaction.

As the said acid-accepting agent, there may be employed any substance which can eliminate an acid without inhibiting the telomerization reaction of TFE. Particularly preferred are, as inorganic compounds, oxides, hydroxides and carbonates of alkali metals (e.g. sodium, potassium), alkaline earth metals (e.g. magnesium, calcium, barium) and zinc, ammonium hydroxide and ammonium carbonate, and as organic compounds alcoholates of alkali metals with methanol or $H(CF_2CF_2)_nCH_2OH$. Organic weak acid salts such as sodium acetate are also effective as the acid-accepting agent, but acetic acid itself may be a telogen in polymerization of TFE to cause undesirable contamination of produced telomers. Similarly, alcoholates of alkali metals with other alcohols than methanol or $H(CF_2CF_2)_nCH_2OH$ also become telogen for TFE, so that a small amount of impurities may be contained in the produced telomers. In case of such contamination being insignificant, however, these substances may be also employed as the acid-accepting agent.

In the telomerization reaction of TFE with methanol of the invention, the addition of the acid-accepting agent into the reaction system may be effected at the time when the reaction rate begins to be reduced after initiation of the reaction, the agent being dissolved or suspended in the starting materials or the reaction product such as methanol and $H(CF_2CF_2)_nCH_2OH$ (n=1-4). Alternatively, the acid-accepting agent may be incorporated into methanol before the reaction. The previous addition prior to the initiation of the reaction is more convenient in respect of reaction operation. When the acid-accepting agent is added before the reaction, in usual, particularly appreciable influence is not observed in the rate of telomerization at the initial stage of the reaction, but the reaction can be continued for extremely long time in comparison with the case of not adding the agent, which causes substantial improvement of the telomer yield.

In usual, a methanol-soluble acid-accepting agent is used as a methanol solution, and a methanol-insoluble agent is employed as a methanol dispersion. The acid-accepting agent may be in powder or granule form and is desired to have a smaller granular degree and a larger specific surface area as much as possible.

The amount of the acid-accepting agent may be $4 \times 10^{-5}$ to $4 \times 10^{-3}$ mol, preferably $2 \times 10^{-4}$ to $2 \times 10^{-3}$ mol, per 1 mol of methanol.

By the addition of the acid-accepting agent into the reaction system in the invention, the reaction time is prolonged to increase the telomer yield, in comparison with the case of not adding the agent. With increase of the telomer yield, in usual, the average molecular weight of the produced telomers tends to be somewhat increased.

The present invention will be hereinafter explained further in detail by the following Examples and Comparative Examples.

Comparative Example 1

Preparation of Telomers by a Conventional Batch Process

In a 3 liter-volume stainless steel autoclave equipped with a stirrer, methanol (1600 g; 50 mol) is charged, and di-t-butyl peroxide (18 g) is added thereto. The air in the reaction vessel is eliminated by a vacuum pump while stirring, and TFE (585 g; 5.85 mol) is introduced therein under pressure. The autoclave is heated to elevate the temperature up to 80° C. With elevation of the inner temperature, the pressure increases to reach 39 kg/cm$^2$ in about 70 minutes and then gradually lowers. After 3 hours, the pressure is reduced to 16 kg/cm$^2$. Then, the autoclave is cooled, and unreacted TFE is recovered. From the amount of the recovered TFE, the amount of reacted TFE is calculated to be about 400 g (4 mol). The reaction product is subjected to rectification to eliminate methanol, whereby a telomer mixture (425 g) is obtained.

Under the same condition but changing the temperature to 100° C. or 120° C., the telomerization reaction is carried out to obtain a telomer mixture.

The thus obtained telomer mixtures are subjected to gas chromatographic analysis to examine the composition of $H(CF_2CF_2)_nCH_2OH$. The results are shown in Table 2.

TABLE 2

| Reaction condition | | Composition of $H(CF_2CF_2)_nCH_2OH$ (% by weight) | | | | | | | |
| --- | --- | --- | --- | --- | --- | --- | --- | --- | --- |
| Temperature (°C.) | Maximum pressure (kg/cm$^2$) | n = 1 | n = 2 | n = 3 | n = 4 | n = 5 | n = 6 | n = 7 | n = 8 |
| 80 | 39 | 5.1 | 16.7 | 17.7 | 18.5 | 16.9 | 14.6 | 7.9 | 2.6 |
| 100 | 42 | 12.1 | 29.4 | 20.0 | 16.6 | 11.4 | 7.3 | 2.8 | 0.4 |
| 120 | 43 | 15.9 | 32.8 | 21.5 | 13.0 | 8.2 | 5.5 | 2.8 | 0.3 |

It is apparent from this Table that, by elevation of the reaction temperature, the average molecular weight is decreased, but the amount of produced telomers of $n \geq 5$ becomes large.

EXAMPLE 1

In a glass pressure autoclave (inner volume, 2000 ml) equipped with a stainless steel stirrer, methanol (800 g; 25 mol) is charged, and diisopropyl peroxydicarbonate (4 g) is added thereto. The inner pressure is reduced by a vacuum pump while stirring until methanol boils. Then, TFE is added to obtain an atmospheric pressure, and the autoclave is heated. When the inner temperature reaches 50° C., the reaction is initiated with introduction of TFE. The reaction pressure is kept to 8 kg/cm$^2$ during the reaction period with continuous introduction of TFE. After 55 minutes, the autoclave is cooled to room temperature, and the reaction product is taken out and subjected to rectification to eliminate methanol, whereby a telomer mixture (211 g) is obtained.

By gas chromatographic analysis, the thus obtained telomer mixture is proved to have the following composition of $H(CF_2CF_2)_nCH_2OH$: n=1, 21.5% by weight;

n=2, 38.2%; n=3, 23.6%; n=4, 10.5%; n=5, 4.1%; n=6, 1.3%; n=7, 0.5%; n=8, 0.3%.

The average molecular weight is 276.9. The amount of produced telomers of n≧5 is much smaller in comparison with Comparative Example 1.

EXAMPLES 2 AND 3

The telomerization reaction of TFE with methanol is carried out in the same manner as in Example 1 but changing the polymerization initiator, the reaction temperature and the reaction pressure. The results are shown in Table 3.

TABLE 3

|  |  | Example 2 | Example 3 |
|---|---|---|---|
| Polymerization initiator |  | t-Butyl peroxy-isobutyrate (5 g) | Di-t-butyl peroxide (20 g) |
| Reaction temperature (°C.) |  | 80 | 110 |
| Reaction pressure (kg/cm$^2$) |  | 8 | 6 |
| Reaction time (min) |  | 43 | 118 |
| Yield of telomers (g) |  | 123 | 135 |
| Telomer composition (% by weight) | n = 1 | 33.9 | 73.5 |
|  | n = 2 | 41.7 | 24.0 |
|  | n = 3 | 17.7 | 2.3 |
|  | n = 4 | 5.2 | 0.2 |
|  | n = 5 | 1.3 | — |
|  | n = 6 | 0.2 | — |
| Average molecular weight |  | 230.6 | 161.0 |

As apparent from this Table, the amount of useful telomers of n≦4 in Example 2 is 98.5% in the total amount of the reaction product, and telomers of n≧5 are not formed in Example 3.

EXAMPLE 4

Into the same autoclave as in Example 1, methanol (800 g) and di-t-butyl peroxide (20 g) are charged, and after closing the autoclave, the inner pressure is reduced while stirring until methanol boils. Then, TFE is added to obtain an atmospheric pressure, and the temperature is elevated up to 125° C. under heating. The reaction is initiated by introducing TFE into the autoclave up to the pressure of 8 kg/cm$^2$. When the pressure is reduced to 7 kg/cm$^2$, TFE is immediately introduced to elevate the pressure to 8 kg/cm$^2$. This cycle of reaction is repeated, whereby an identical amount of TFE is introduced at each cycle and at the same time an identical amount of telomers is produced. The reaction time at every 10 cycles after initiation of the reaction is as shown in Table 4.

TABLE 4

| Reaction cycle | 10 | 20 | 30 | 40 | 50 | 60 | 70 |
|---|---|---|---|---|---|---|---|
| Reaction time | 16'50" | 33'45" | 51'10" | 71'5" | 94'55" | 128' | 180'50" |

After 70 cycles of reaction, the autoclave is cooled to room temperature, and TFE is released. The collected reaction product shows a pH value of 2.5. For elimination of methanol, the product is subjected to distillation to obtain a telomer mixture (215 g).

By gas chromatographic analysis, the thus obtained telomer mixture is proved to have the following composition of H(CF$_2$CF$_2$)$_n$CH$_2$OH: n=1, 82.5% by weight; n=2, 15.2%; n=3, 1.5%; n=4, trace.

Telomers of n≧5 are not detected, and the average molecular weight is 150.5.

EXAMPLES 5 TO 8

Figure 2:
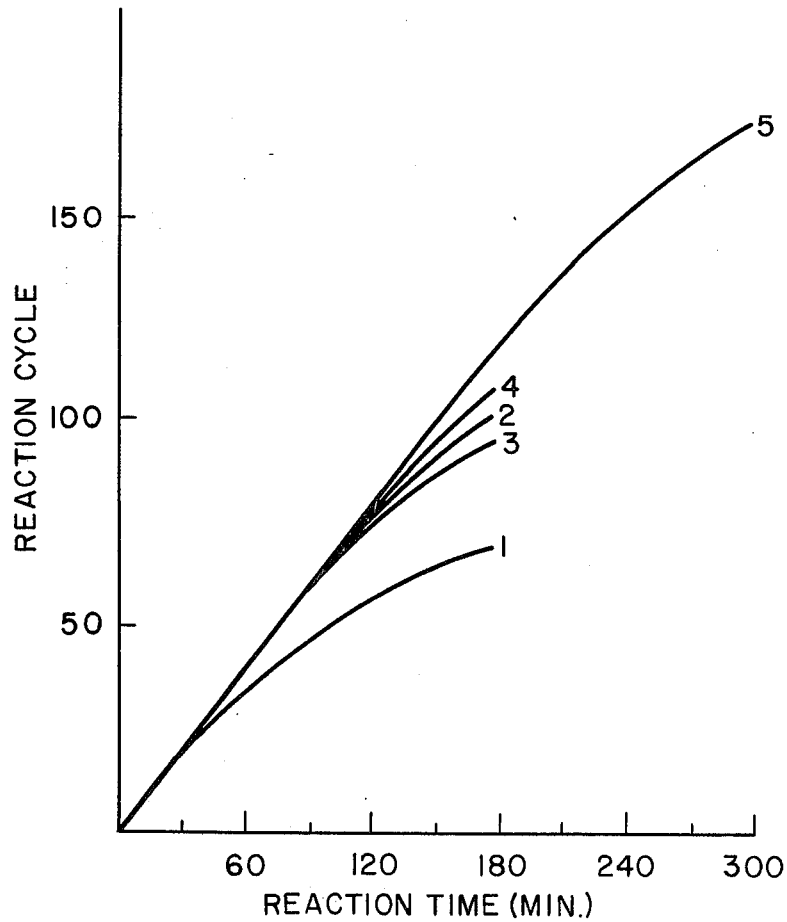

The telomerization of TFE is carried out under the same conditions as in Example 4 except that an acid-accepting agent (ZnO, CaO or (NH$_4$)$_2$CO$_3$) is previously incorporated into methanol. The reaction conditions and the results in these cases including Example 4 in which no acid-accepting agent is used are shown in FIG. 2 and Table 5, respectively. In FIG. 2, 1, 2, 3, 4, and 5 correspond respectively to the results in Examples 4, 5, 6, 7, and 8.

As understood from FIG. 2, the initial reaction rate is not influenced by the addition of various acid-accepting agents. But, in the case that the acid-accepting agent is used, decrease of the reaction rate with lapse of time is prevented, and the average reaction rate and the yielded are improved in comparison with the case in which no acid-accepting agent is used. By the increase of the amount of CaO to be added, notable effect of prevention of decrease of reaction rate is obtained, and the telomer yield can be increased by prolongation of the reaction time.

In all of the cases shown in the following Table, formation of components of n≧5 is not observed.

TABLE 5

| Example No. | Acid-accepting agent | Reaction time | Reaction cycle | Average reaction rate (cycle/min) | pH in reaction system after reaction | Yield of telomers (g) | Average molecular weight |
|---|---|---|---|---|---|---|---|
| 4 | Not added | 180'50" | 70 | 0.39 | 2.5 | 215 | 151 |
| 5 | (NH$_4$)$_2$CO$_3$H$_2$O (1.14 g; 1/100 mol) | 132'30" | 80 | 0.60 | 3.5 | 242 | 150 |
| 6 | ZnO (0.81 g; 1/100 mol) | 178'30" | 95 | 0.53 | 3 | 296 | 152 |
| 7 | CaO (0.56 g; 1/100 mol) | 179' | 105 | 0.59 | 3 | 316 | 151 |
| 8 | CaO (1.12 g; 2/100 mol) | 294'50" | 170 | 0.58 | 3 | 494 | 153 |

EXAMPLES 9–11 AND REFERENCE EXAMPLES 1-4

The telomerization reaction of TFE is carried out under the same conditions as in Example 4 except that a compound as acid-accepting agent (1/100 mol) is previously incorporated into methanol. The reaction cycles and the reaction times in these cases including Example 4 in which no acid-accepting agent is added are shown in Table 6.

TABLE 6

| | Kind and amount of acid-accepting agent (g) | Cumulative reaction time at every 10 cycles | | | | | | | |
|---|---|---|---|---|---|---|---|---|---|
| | | 10 | 20 | 30 | 40 | 50 | 60 | 70 | 80 |
| Example 4 | Not added | 16'50" | 33'45" | 51'10" | 71'5" | 94'55" | 128' | 180'50" | — |
| Example 9 | MgO (0.4) | 12'7" | 25' | 35'55" | 48'40" | 67'15" | 90' | 114'30" | 138'30" |
| Example 10 | BaCO$_3$ (1.97) | 15'45" | 32'25" | 48' | 65'40" | 81'49" | 100'40" | 120' | 139'27" |
| Example 11 | CH$_3$COONa (0.86) | 12' | 27'5" | 44'40" | 64'25" | 88' | 113'40" | 142'45" | 173' |
| Reference Example 1 | Al$_2$O$_3$ (1.1) | 15'35" | 33' | 51'55" | 76'12" | 111'10" | 168' | — | — |
| Reference Example 2 | SiO$_2$ (0.6) | 17' | 35'5" | 78'40" | 103'28" | 133'18" | 164'15" | — | — |
| Reference Example 3 | Fe$_2$O$_3$ (1.6) | 16'40" | 30'50" | 56' | 83'30" | 126'49" | 175' | — | — |
| Reference Example 4 | CuO (0.8) | Reaction is stopped after 5 cycles. | | | | | | | |

It is understood from this Table that, by addition of MgO, CaCO$_3$, BaCO$_3$ or CH$_3$COONa into the reaction system, the rate of the reaction is maintained favorably in a prolonged reaction period in comparison with the case of not adding the acid-accepting agent. The compounds used in Reference Examples (Al$_2$O$_3$, SiO$_2$, Fe$_2$O$_3$ and CuO) do not exhibit any appreciable effect or rather inhibit the reaction.

EXAMPLES 12–14

In a stainless steel autoclave equipped with a stirrer (inner volume, 2000 ml), methanol (800 g), di-t-butyl peroxide (20 g) and a varied amount of an acid-accepting agent are charged, and after closing the autoclave, the inner pressure is reduced while stirring until methanol boils. Then, TFE is introduced therein to obtain a normal pressure, and the temperature is immediately elevated. When the temperature reaches 125° C., the TFE is pressured to 8 kg/cm$^2$ to initiate the reaction. When the pressure is reduced to 7 kg/cm$^2$, TFE is immediately introduced to elevate the pressure up to 8 kg/cm$^2$, and thus this cycle of reaction is repeated. The reaction time at every 10 cycles after initiation of the reaction is as shown in Table 7.

TABLE 7

| | Acid-accepting agent (g) | Cumulative reaction time at every 10 cycles | | | | | | | | Final pH value |
|---|---|---|---|---|---|---|---|---|---|---|
| | | 10 | 20 | 30 | 40 | 50 | 60 | 190 | 200 | |
| Example 12 | Not added | 15' | 30'42" | 49'55" | 73'20" | 102'55" | 142'20" | — | — | 2 |
| Example 13 | CaCO$_3$ (1) | 13'36" | 27'30" | 40'45" | 54'5" | 67'38" | 81'4" | 340'10" | 394'5" | 3 |
| Example 14 | CaO (1.12) | 18'55" | 36'45" | 51'19" | 66' | 80'33" | 94'50" | 365' | — | 3 |

As understood form this Table, the rate of telomerization reaction is greatly decreased at approximately the 40th cycle when no acid-accepting agent is added, while by addition of CaCO$_3$ or CaO as the acid-accepting agent the reaction can be continued for a prolonged time without decreasing the rate of the reaction.

EXAMPLES 15–18

Figure 3:
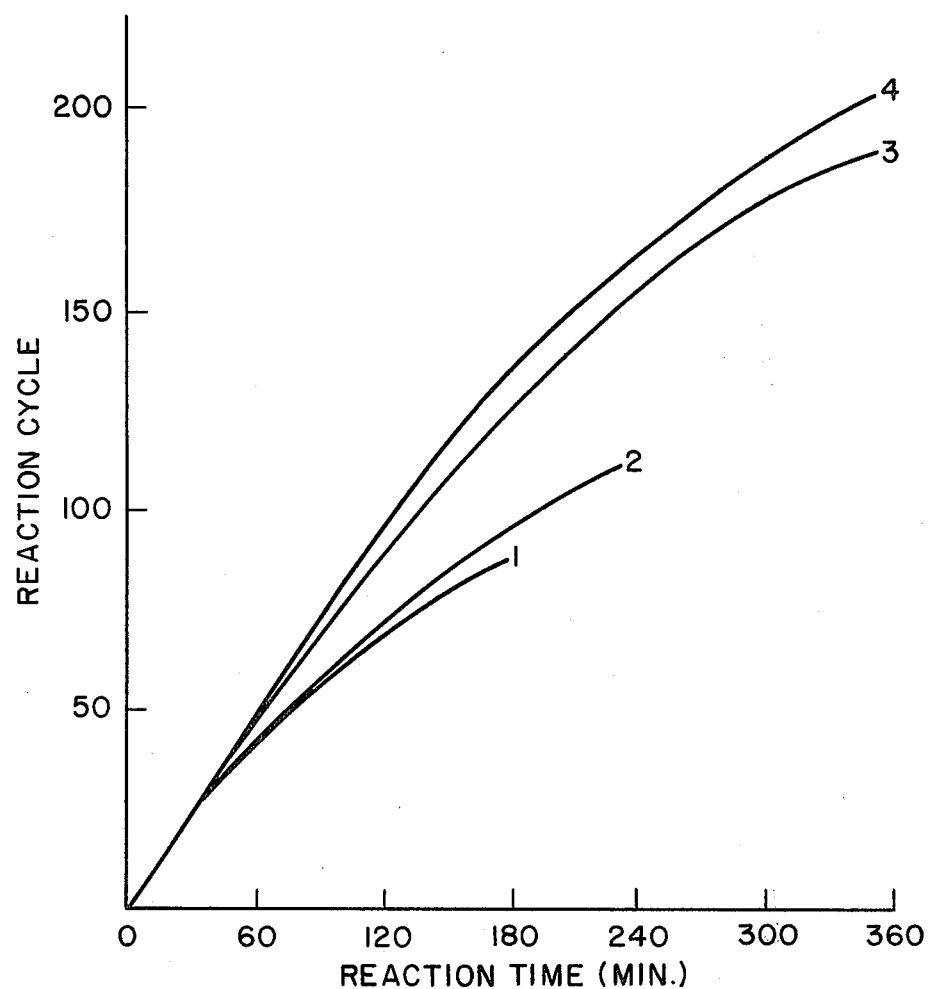

In a glass autoclave equipped with a stirrer (inner column, 1850 ml), methanol (800 g; 25 mol), di-t-butyl peroxide (20 g) and a varied amount of CaCO$_3$ are charged, and after closing the autoclave, the inner pressure is reduced while stirring until methanol boils. Then, TFE is introduced therein to obtain an atmospheric pressure, and the temperature is immediately elevated. When the temperature reaches 125° C., the TFE pressure is elevated to 8 kg/cm$^2$ to initiate the reaction. When the pressure is reduced to 7 kg/cm$^2$, TFE is immediately introduced to elevate the pressure up to 8 kg/cm$^2$, and thus this cycle of reaction is repeated. The reaction conditions and the results in these cases are shown in FIG. 3 and Table 8. In FIG. 3, 1, 2, 3, and 4 correspond respectively to the results in Examples 15, 16, 17 and 18.

TABLE 8

| Example No. | Acid-accepting agent | Reaction time | Reaction cycles | pH after reaction | Yield of telomers (g) |
|---|---|---|---|---|---|
| 15 | Not added | 179'29" | 86 | 2.5 | 219 |
| 16 | CaCO$_3$ (0.5 g; 5/1000 mol) | 240' | 110 | 3 | 284 |
| 17 | CaCO$_3$ (1 g; 1/100 mol) | 361'40" | 186 | 3 | 475 |
| 18 | CaCO$_3$ (2 g; 2/100 mol) | 355'12" | 200 | 3 | 508 |

As apparent from Table 8 and FIG. 3, an effect for prevention of decrease of the reaction rate is obtained by the addition of 0.5 g of CaCO$_3$ ($2 \times 10^{-4}$ mol per 1 mol of methanol), and this effect becomes more notable by the addition of 1 g ($4 \times 10^{-4}$ mol per 1 mol of methanol) and 2 g ($8 \times 10^{-4}$ mol per 1 mol of methanol) of this acid-accepting agent.

EXAMPLES 19 AND 20

The telomerization reaction of TFE and methanol is carried out as in Example 4. At the 30th cycle after initiation of the reaction, a methanol solution (10 ml) containing KOH (0.56 g) or CH$_3$ONa (0.54 g) (1/100 mol as KOH or CH$_3$ONa) is added to the autoclave under pressure, and the reaction is further continued. The cumulative reaction time at every 10 cycles is as shown in Table 9.

TABLE 9

| Reaction cycles | | 10 | 20 | 30 | 40 | 50 | 60 | 70 |
|---|---|---|---|---|---|---|---|---|
| Reaction | Example 19 | 16'5" | 32'10" | 51'00" | 66'43" | 82'17" | 99'21" | 118'30" |

TABLE 9-continued

| Reaction cycles | | 10 | 20 | 30 | 40 | 50 | 60 | 70 |
|---|---|---|---|---|---|---|---|---|
| time | Example 20 | 17'10" | 34'25" | 52'50" | 67'40" | 82'35" | 98'32" | 115'02" |

It is understood from this Table that the decreased reaction rate is recovered to the initial level by the addition of KOH or CH$_3$ONa.

EXAMPLE 21

In a 40 liter-volume stainless steel autoclave equipped with a stirrer, methanol (15.2 kg; 475 mol), t-butyl peroxide (500 g) and CaCO$_3$ (70 g; 0,7 mol) are charged, and after closing the autoclave, the inner pressure is reduced while stirring until methanol boils and the air is eliminated. Then, TFE is added to obtain an atmospheric pressure, and the temperature is elevated up to 122.5° C., when TFE is immediately introduced to elevate the pressure to 7.5 kg/cm$^2$, and the reaction is initiated. During the reaction, the pressure is kept at this level with continuous introduction of TFE. After 6 hours of reaction, the autoclave is cooled to room temperature, and TFE is released. The reaction product is taken out and subjected to rectification for elimination of methanol, whereby a telomer mixture (14 kg) is obtained. By analysis, the thus obtained telomer mixture is proved to have the following composition of H(CF$_2$CF$_2$)$_n$CH$_2$OH: n=1, 80.1%; n=2, 18.1%; n=3, 1.6% n=4, 0.2%. Telomers of n≧5 are not detected.

What is claimed is:

1. A process for preparing by telomerization a fluoroalkanol which is predominantly of the formula $$H(CF_2CF_2)_nCH_2OH$$

wherein n is an integer of not more than 4, said process comprising mixing substantially the total amount of methanol and polymerization initiator required for the telomerization together and then mixing tetrafluoroethylene with the resulting mixture at a rate whereby the temperature of the resulting reaction mixture is maintained at from 25° to 150° C., the partial pressures of tetrafluoroethylene and methanol are between 30 to 1 and 1 to 5 and the total pressure on the reaction is between 1 and 12 kg per cm$^2$ gauge until telomerization is completed.

2. The process of claim 1 wherein the total volume of methanol reacted with the tetrafluoroethylene and the said initiator are placed in a reaction vessel prior to mixing with tetrafluoroethylene and the tetrafluoroethylene is added continuously without interruption for reaction under said temperature and pressure conditions.

3. The process of claim 1 wherein the total volume of methanol reacted with the tetrafluoroethylene and said initiator are placed in a reaction vessel prior to mixing with tetrafluoroethylene and the tetrafluoroethylene is added intermittently at spaced intervals of time.

4. The process of claim 1 wherein the reaction is carried out at a partial pressure ratio of tetrafluoroethylene and methanol of 30/1 to 1/5 under the conditions of pressure and temperature within the area (A, B, C, D and E) in FIG. 1.

5. The process of claim 1 wherein an acid-accepting agent is present in the reaction system.

6. The process of claim 5, wherein the acid-accepting agent is present in an amount of $4\times10^{-5}$ to $4\times10^{-3}$ mol per 1 mol of methanol.

7. The process of claim 5 wherein the acid-accepting agent is a member selected from the group consisting of oxides, hydroxides and carbonates of alkali metals, alkaline earth metals and zinc, alkali metal alcoholates and ammonium hydroxide and ammonium carbonate.

* * * * *